United States Patent [19]

Kempster et al.

[11] Patent Number: 4,775,516

[45] Date of Patent: Oct. 4, 1988

[54] APPARATUS FOR MONITORING THE CARBON CONTENT OF BOILER FLUE ASH

[75] Inventors: Roger D. Kempster, Betchworth; Peter A. E. Crosse, Great Bookham, both of United Kingdom

[73] Assignee: Central Electricity Generating Board, London, United Kingdom

[21] Appl. No.: 915,236

[22] Filed: Oct. 3, 1986

[30] Foreign Application Priority Data

Oct. 4, 1985 [GB] United Kingdom ............... 8524503

[51] Int. Cl.$^4$ ............... B65G 27/04; B65G 27/08; B65G 27/32
[52] U.S. Cl. ............................. 422/80; 422/62; 422/145; 422/219; 110/101 R; 110/113; 198/371; 198/753; 222/344; 222/363; 414/221
[58] Field of Search ............. 422/62 X, 145 X, 219 X, 422/80; 110/101 R X, 113 X; 222/55, 56, 63, 344 X, 363 X; 251/5; 198/371 X, 753 X; 414/217, 221 X

[56] References Cited

U.S. PATENT DOCUMENTS

| | | | |
|---|---|---|---|
| 2,633,154 | 3/1953 | Eastman | 251/5 |
| 2,734,526 | 2/1956 | Aagaard | 251/5 |
| 3,365,240 | 1/1968 | Gordon | 406/169 |
| 3,426,853 | 2/1969 | Del Rosso | 222/363 |
| 3,454,307 | 7/1969 | Bishop | 406/169 |
| 3,607,071 | 9/1971 | Staffin et al. | 23/230 PC |
| 3,745,668 | 7/1973 | Vian-Ortuno et al. | 34/57 A |
| 3,921,307 | 11/1975 | Marek et al. | 34/10 |
| 4,171,067 | 10/1979 | Faulkner et al. | 222/77 |
| 4,513,882 | 4/1985 | Cabi-Akman | 222/56 |

FOREIGN PATENT DOCUMENTS

| | | | |
|---|---|---|---|
| 513821 | 9/1952 | Belgium | 251/5 |
| 1014043 | 8/1952 | France | 251/5 |
| 1027948 | 4/1958 | Fed. Rep. of Germany | 251/5 |
| 2143172 | 2/1973 | Fed. Rep. of Germany | . |
| 2809367 | 9/1979 | Fed. Rep. of Germany | 198/753 |
| 2912681 | 10/1980 | Fed. Rep. of Germany | 198/753 |
| 3303612 | 8/1983 | Fed. Rep. of Germany | . |
| 2022765 | 12/1979 | United Kingdom | . |

OTHER PUBLICATIONS

Patent Abstracts of Japan, vol. 7, No. 64 (P-183) (1209), Mar. 17, 1983.

Primary Examiner—Barry S. Richman
Assistant Examiner—Lynn M. Kummert
Attorney, Agent, or Firm—Willian Brinks Olds Hofer Gilson & Lione Ltd.

[57] ABSTRACT

A carbon-in-ash monitor uses a fluidized bed furnace to burn any carbon in sampled boiler flue ash and evolve carbon dioxide therefrom. Fluidizing gas (air) is provided to the bed a measured flow rate and a batching arrangement feeds successive batches of ash of measured mass to the furnace at a measured frequency. A $CO_2$ monitor measures the amount of $CO_2$ evolved to determine the carbon content of the ash. Batches are provided using a vibratory table to transport ash from a point of supply to the table and a point of delivery of ash in a stream from the table. The vibratory table is horizontal and is driven so that the mode of vibration can be selected to reverse the direction of ash transport.

12 Claims, 7 Drawing Sheets

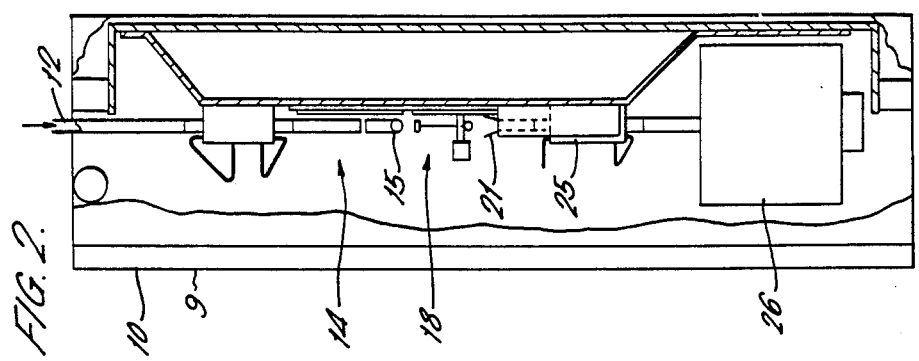
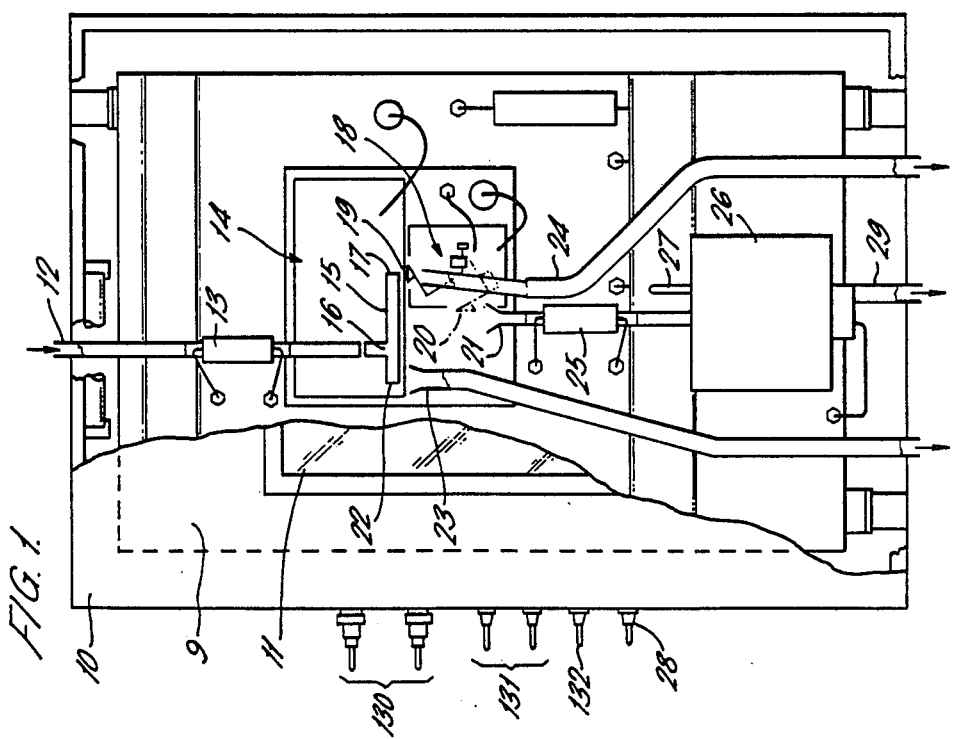

APPARATUS FOR MONITORING THE CARBON CONTENT OF BOILER FLUE ASH

BACKGROUND OF THE INVENTION

1. The Field of the Invention

The present invention is concerned with apparatus for monitoring the carbon content of boiler flue ash.

In coal fired power stations it is normal to use pulverised fuel to ensure efficient combustion. Nevertheless some of the the combustible material in the fuel may not be burnt. The ash resulting in such power stations comprises very fine particulate material, some of which is entrained in the combustion gases flowing through the boiler flue. Such ash is typically removed from the flue gases discharged by the power station by filters and electrostatic separators.

It is useful to be able to determine the efficiency of combustion in a power station boiler and one way of doing this is to determine the level of carbon remaining in such boiler flue ash.

2. Prior Art

Reference should be made to Laboratory Note No. Rd/L/N 101/77 of Central Electricity Research Laboratories, Leatherhead, United Kingdom. This Note is entitled "C.E.R.L. On-Line Carbon-in-Ash Monitor", by J. E. Roughton and W. L. Snowsill, and is dated 8th Aug. 1977. The Note has been available since September 1977 to interested members of the public on request from the Central Library of the Central Electricity Generating Board, Sudbury House, 14 Newgate Street, London, EC1A 7 AU.

The above referred Laboratory Note discloses a carbon-in-ash monitor employing a fluidised bed furnace to burn any carbon in sampled boiler flue ash and evolve carbon dioxide therefrom. Fluidising gas is provided to the fluidised bed at a measured flow rate and a batching arrangement feeds successive batches of ash of measured mass to the furnace at a measured frequency. The amount of $CO_2$ evolved is then monitored to determine the carbon content of the ash. The apparatus operates with successive batches of ash delivered to the furnace so that the level of carbon in the ash flowing in the boiler flue can be monitored substantially continuously. The total response time of the apparatus, from drawing a sample of ash from the flue gas, to providing an indication of the carbon content of that ash, is from one to two minutes. Successive batches of ash can be delivered to the fluidised bed at typically 30 second intervals. The time taken for a particular batch of ash to be completely burned in the fluidised bed is less than 30 seconds.

Conveniently batches of constant mass are delivered at a constant rate and the flow rate of fluidising gas, typically air, through the fluidised bed is also maintained constant, so that analysis of the carbon dioxide concentration in the gas leaving the fluidised bed provides a direct measure of the carbon content of the ash.

The batches are provided using a vibratory table to transport ash from a point of supply from the flue sampler, so as to be delivered in a stream from the table to a batch collector.

In the described arrangement, the batch collector is an over-centre stable balance arm with a collection bucket at one end located to collect ash from the stream delivered from the vibratory table. When the amount of ash collected in the bucket exceeds a preset mass, the arm over balances, taking the bucket out of the ash stream and depositing the batch in a collection funnel. Remaining ash on the vibratory table continues to flow in the stream from the table to waste.

It has proved difficult with this arrangement to provide accurately controlled batch sizes. Further the waster ash from the vibratory table tends to foul the balance mechanism.

BRIEF SUMMARY OF THE INVENTION

According to the present invention there is provided apparatus for monitoring the carbon content of boiler flue ash comprising ash receiving means to receive ash sampled from a boiler flue, a fluidised bed furnace to burn any carbon in the ash to evolve carbon dioxide, gas flow means to provide a measured flow rate of fluidising gas to the fluidised bed, a carbon dioxide analyzer providing an indication of carbon dioxide concentration, feeding means to feed gas including the evolved carbon dioxide from the fluidised bed to the analyser, and batching means to deliver batches of ash of measured mass to the furnace at a measured frequency, the batching means including a vibratory table for transporting ash between a point of supply of the ash to the table from the ash receiving means to a point of delivery of the ash in a stream from table, and collecting means for collecting said stream to provide said batches, wherein said vibratory table is horizontal in the direction of transport and includes direction selecting means to change the mode of vibration of the table to reverse the direction of transport of ash on the table.

With the arrangement of the invention, the stream of ash from the vibratory table can be halted by changing the mode of vibration, so that the batching of the ash can be more closely controlled and fouling alleviated.

The manner in which a change in vibrational mode of the table can reverse the direction of transport of ash along a horizontal table will be described in more detail later herein.

The vibratory table may include a waste point on the side of the supply point remote from said delivery point, whereby ash on the table can be transported to said waste point, during said reversed direction of transport, for collection from the table.

Conveniently said vibratory table comprises a horizontal delivery table, an intermediate support, first mounting means mounting the table on the intermediate support for oscillatory movement of the table relative to the intermediate support only in a first substantially linear direction parallel to the delivery direction, a fixed support, second mounting means mounting the intermediate support on the fixed support for oscillatory movement of the intermediate support relative to the fixed support only in a second substantially linear direction in a vertical plane and orthogonal to said first direction, vibrating means to apply said oscillatory movements at a common frequency, and control means for changing the relative phase of the oscillatory movements to reverse the direction of transport of particulate material on the delivery table.

Preferably said batching means comprises means determining when a predetermined mass of ash, representing one said batch of measured mass, is collected in said collecting means and, in response thereto, halting further collection of ash in the collecting means.

Very conveniently, said means determining when a predetermined mass of ash is collected is effective to operate said direction selecting means to reverse the direction of transport when said predetermined mass of ash is collected.

In a preferred embodiment the apparatus includes airlock means to deliver ash from the ash receiving means to the batching means.

The air lock means may be constituted by an air lock valve comprising first and second lengths of flexible tube in series connected to conduct ash by gravity from the receiving means to the batching means, the first length being located above the second length, first and second collars defining respective closed annular spaces around the first and second lengths of tube whereby fluid pressure within one of the annular spaces can collapse the respective length of tube to seal the length, and means for applying said fluid pressure to the two annular spaces alternately so that one length of tube is always sealed.

Conveniently, the lengths of tube are formed to have cross-sections with diametrically opposed acute angled internal corners, whereby the lengths of tube can collapse flat under external fluid pressure to completely seal the respective length.

There may be a further said air lock means to deliver said measured batches from said batching means to the furnace.

In one embodiment, the apparatus may include acceleration responsive means providing an indication of the acceleration amplitude of the vibratory table, and means determining the difference in said indication between the start and finish of delivery from the table of a batch of ash collected in said collecing means to measure the mass of the batch.

Features of the preferred embodiments of this invention are also applicable more generally than to the above described apparatus for monitoring the carbon content of boiler flue ash. Accordingly, in a further aspect of the invention, a vibratory table for transporting particulate material comprises a delivery table which is flat in a delivery direction, an intermediate support, first mounting means mounting the table on the intermediate support for oscillatory movement of the table relative to the intermediate support only in a first substantially linear direction parallel to the delivery direction, a fixed support, second mounting means mounting the intermediate support on the fixed support for oscillatory movement of the intermediate support relative to the fixed support only in a second substantially linear direction in a vertical plane and orthogonal to said first direction, vibrating means to apply said oscillatory movements at a common frequency, and control means for changing the relative phase of the oscillatory movements to reverse the direction of transport of particulate material on the delivery table.

In a further aspect, the invention provides an air lock valve for delivering a flowable medium by gravity between regions of differing ambient gas pressure, comprising first and second lengths of flexible tube in series for conducting the fluid by gravity between the regions, the first length being located above the second length, first and second collars defining respective closed annular spaces around the first and second lengths of tube whereby fluid pressure within one of the annular spaces can collapse the respective length of tube to seal the length, and means for applying said fluid pressure to the two annular spaces alternately so that one length of tube is always sealed.

Preferably the lengths of tube are formed to have cross-sections with diametrically opposed acute angled internal corners, whereby the lengths of tube can collapse flat under external fluid pressure to completely seal the respective length.

In a still further aspect of the present invention, batch weighing apparatus for delivering sample batches of a particulate material and determining the mass of the batches comprises a vibratory table for transporting the particulate material between a point of supply of the material on to the table and a point of delivery of the material from the table, supply means to supply on to the table a set quantity of the material in excess of the batch mass to be determined, collecting means to collect from the table material of said quantity which is transported to the point of delivery, acceleration responsive means providing an indication of the acceleration amplitude of the vibratory table, and means determining the difference in said indication between the start and finish of delivery from the table of a batch of the material collected in said collecting means. By monitoring the change in the amplitude of acceleration of the vibratory table, under constant driving force, as material from a set quantity originally supplied to the table is delivered from the table at the point of delivery, the mass of material that has been delivered can be measured. As material is delivered from the table, the effective mass of the table with its load of particulate material falls with a resultant increase in the acceleration amplitude. This provides a very convenient method of determining the mass of material being delivered by the table.

It will be appreciated that the above apparatus has particular application in the carbon-in-ash monitoring apparatus described above, to replace the batch weighing apparatus in the embodiment previously mentioned.

The apparatus may include means for stopping further delivery of material from the table to terminate collection of the batch in the collecting means. Thus, the batch may comprise less than the total quantity of the material originally supplied to the table at the point of supply. In particular said means for stopping may comprise means to halt further transport of material on the table to the delivery point. For this purpose, the vibratory table may be horizontal in the direction between the point of supply and the point of delivery and said means to halt further transport to the delivery point may comprise means to change the mode of vibration of the table to reverse the direction of transport of material on the table.

Conveniently then, the apparatus includes a waste point along the table on the side of the supply point remote from said delivery point, whereby material of said quantity remaining on the table after delivery of the batch is transported back along the table to said waste point, and means to collect from the table material transported to the waste point.

In a preferred example, control means is provided responsive to said indication of acceleration amplitude to stop further delivery of material from the delivery point of the table on determining that a predetermined mass of said material has been delivered.

Examples of the present invention will now be described in more detail with reference to the accompanying drawings.

BRIEF DESCRIPTION OF THE DRAWINGS

FIG. 1 is a schematic view in elevation of a carbon-in-ash monitoring apparatus embodying the present invention;

FIG. 2 is a view in elevation of the apparatus of FIG. 1 from one side;

FIG. 12 is a graphical representation of the changes in acceleration amplitude of a vibratory table used for measuring the mass of batches of ash delivered to the fluidised bed in an alternative embodiment of the present invention.

DESCRIPTION OF THE PREFERRED EMBODIMENTS

Figure 3:
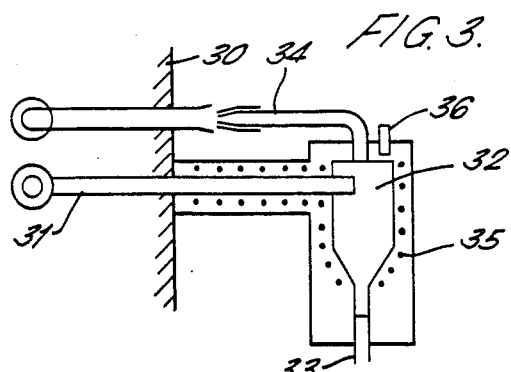
FIG. 3 is a schematic representation of apparatus for drawing samples of fly-ash from a flue for delivery to the monitoring apparatus of FIGS. 1 and 2.

Referring to FIGS. 1 and 2, the monitoring apparatus illustrated comprises a casing 10 which has a viewing window 11 in the front panel 9. The front panel 9 is cut away in FIG. 1 to show the location of various of the internal components. Ash sampled from a boiler flue or duct is fed into the cabinet through conduit 12 via an air lock valve 13 to a batch weighing mechanism shown generally at 14. The air lock valve 13 permits the ash to be supplied from a region of below atmospheric pressure in conduit 12, to the batch weighing mechanism 14 which operates at atmospheric pressure.

The batch weighing mechanism 14 includes a vibratory table 15 formed as a horizontal tube into which quantities of ash are fed from the air lock valve 13 at a supply point 16 intermediate the ends of the tube. The tube 15 is open at both ends and the mechanism for vibrating the tube 15 can be controlled to select modes of vibration which cause ash deposited in the tube to be transported either forwards or backwards along the tube. In the forward direction, ash within the tube is transported and spread out somewhat along the length of the tube to emerge as a stream from an end 17 of the tube (the righthand end as illustrated in FIG. 1). This is the delivery end of the tube. Beneath end 17 of the tube, there is mounted on over-centre stable balance arm, indicated generally at 18, which has a collection bucket 19 substantially at one end of the arm. When the collection bucket 19 is empty, the balance arm can come to rest in the position as illustrated in FIG. 1 with the bucket 19 located immediately beneath the end 17 of the tube 15 so that the stream of ash from the end 17 falls into the bucket 19. When a certain mass of ash has collected inthe bucket 19, the balance arm overbalances causing the bucket 19 to swing downwards and to the left in FIG. 1 to the position shown in dotted lines at 20, whereupon the batch of ash contained in the bucket is deposited into a funnel 21.

At the same time, sensors which will be described in more detail later, detect the overbalancing of the arm 18 and cause the mode of vibration of the tube 15 to be changed to reverse the direction of transport of ash in the tube. Thus remaining ash within the tube 15 is transported back along the tube, to the left in FIG. 1, to the opposite end 22 of the tube to be deposited in a waste pipe 23. It will be appreciated that some small amount of ash may be spilled from the delivery end 17 of the tube as the bucket 18 swings away from the collecting position before the reversing of the vibratory table carried the remaining ash back to the opposite end of the tube. This spilled ash is collected at the open end of an additional waste tube 24.

The batch weighing apparatus illustrated at 14 thereby provides batches of ash of substantially equal mass and delivers these to the funnel 21. These batches of ash are then fed successively through a further air lock valve 25 into a fluidized bed 26. The fluidised bed 26 comprises a bed of ash which is fluidised by a constant volume flow of air driven up through the bed. The bed is maintained at a temperature sufficient to burn off any carbon contained in ash delivered to the bed, evolving carbon dioxide. Appropriate temperatures range from between about 700° C. up to 900° C. for certain kinds of ash. The timing of the apparatus is made such that all the carbon contained in the ash of a particular batch delivered to the fluidised bed is burnt off and carried away from the fluidised bed before the next batch of ash is delivered to the bed.

The fluidising air with carbon dioxide evolved in the bed is carried from the bed along a conduit 27 which leaves the cabinet 10 at a union 28. The gas from the fluidised bed is fed to a carbon dioxide analyser, not shown in FIG. 1, to determine the concentration of carbon dioxide. In this way the amount of carbon dioxide evolved in burning the measured mass of ash enables the amount of carbon in the ash to be determined. As additional batches of ash are added to the fluidised bed 26, excess ash in the bed is allowed to spill over a weir to waste, via a pipe 29, to keep the level of the fluidised bed substantially constant.

Various components of the apparatus illustrated in FIGS. 1 and 2 and also of anciliary apparatus will now be described in more detail.

FIG. 3 illustrates a sampling system for sampling flue gases and separating fly-ash therefrom for delivery to the cabinet of FIGS. 1 and 2 along the conduit 12. Flue gas with entrained ash particles is drawn from a flue duct 30 along a pipe 31 into a cyclone separator 32. In the cyclone 32, ash is separated from the flue gas, falling to the bottom of the cyclone to flow out through pipe 33 which is connected to the inlet pipe 12 of the cabinet 10. The flue gas is returned from the cyclone 32 by means of pipe 34. The cyclone sample 32 and the pipe 31 supplying flue gas with ash entrained to the sampler are heated using electrical heating elements 35 to maintain the temperature of the gas and ash in the cyclone substantially at the flue temperature. Furthermore, a rapper 36 is provided to strike the cyclone vessel at intervals of say half a minute, to shake ash which may have accumulated on the walls of the cyclone and assist flow down the pipe 33. Cyclone separators of this general kind are already known and used in other applications for sampling fly ash in flue gases.

Figure 4:
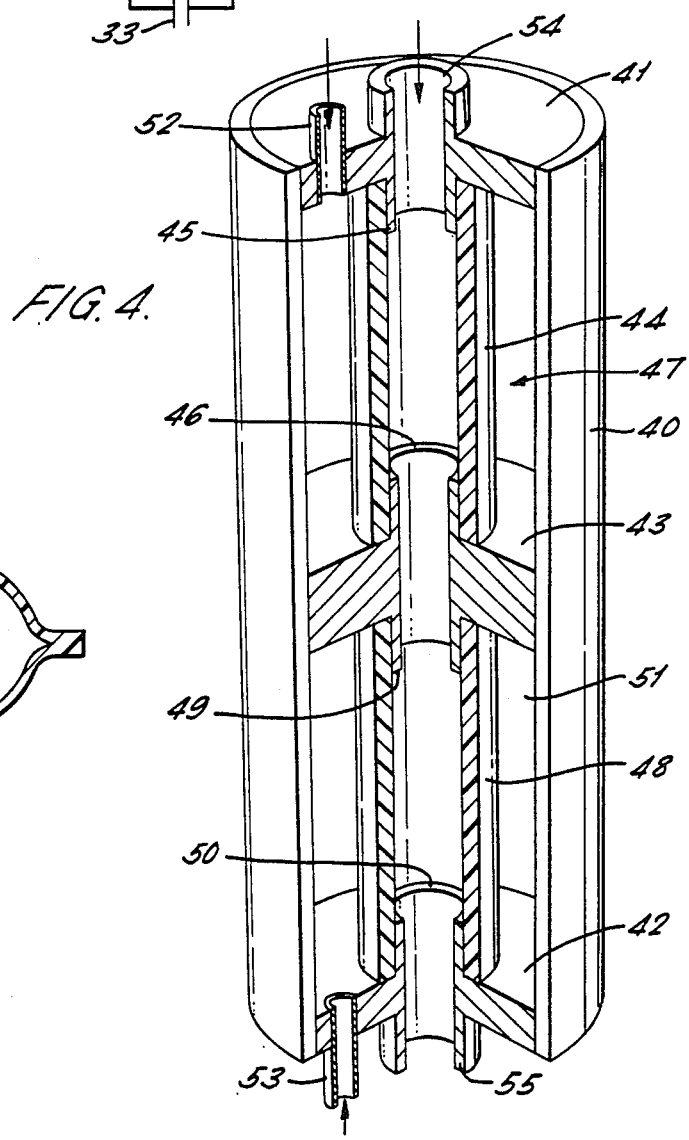
FIG. 4 is a view partly in cross section of an air lock valve for use in the apparatus of FIGS. 1 and 2.

FIG. 4 illustrates a preferred embodiment of air lock valve to permit ash to be carried by gravity between regions of different gas pressure. In the carbon-in-ash monitor described, the ash sampling cyclone (FIG. 3) typically operates at a pressure somewhat below atmospheric so that the gas pressure in the pipe 33 from the sampler, and in the feed conduit 12 into the cabinet of FIG. 1 is also below atmospheric.

The air lock valve of FIG. 4 comprises an outer rigid cylinder 40 sealed at each end to annular discs 41 and 42. A third annular disc 43 is sealed substantially midway between the ends of the outer cylinder 40. A length 44 of flexible tubing is mounted between nipples 45 and 46 extending centrally from the facing annular surfaces of the discs 41 and 43 respectively. There is thus formed a closed annular space 47 bounded on the inside by the flexible tube 44 and on the outside by a collar formed by the upper (in FIG. 4) portion of the cylinder 40.

Similarly, a second length of flexible tubing 48 is mounted between nipples 49 and 50 extending centrally from facing annular surfaces of the discs 43 and 42 respectively, again forming an annular space 51 between the flexible tube 48 and a collar formed by the lower part of the cylinder 40.

Figure 5:
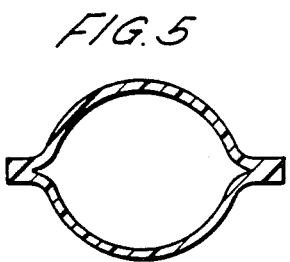
FIG. 5 is a cross-sectional view of the profile of the collapsable tubes used in the air lock valve of FIG. 4.

The annular spaces 47 and 51 can be independently pressurised by the application of a pressurised fluid, typically air, through connection nipples 52 and 53 respectively extending outwardly of the end discs 41 and 42. When air pressure is applied to one of the annular spaces 47 and 51, the corresponding length (44 or 48) of flexible tubing is caused to collapse inwardly to seal off the flow passage through the tube. For this purpose, the flexible tube may be formed with a special cross sectional profile to encourage the tube to collapse flat to seal the tube, under external over pressure. A suitable cross-section is illustrated in FIG. 5.

In operation as an air lock when delivering ash by gravity from an inlet 54 to an outlet 55 of the valve, at least one of the spaces 47 and 51 is always pressurised to hold its respective length of flexible tube sealed. As a result there is no open passage for gas flow in the reverse direction upwards through the valve to the region of lower than atmospheric pressure in the cyclone sampler. The normal sequence of operating the valve can be considered to start with both spaces 47 and 51 pressurised to seal both lengths of flexible tube. The upper space 47 is then unpressurised permitting ash to fall through the inlet 54 to accumulate inside the annular disk 43 above the sealed portion of flexible tube length 48. The space 47 is then repressurised to seal the tube length 44 again and subsequently the lower space 51 is unpressurized permitting the ash to fall out through the outlet 55. Thereafter the space 51 is again pressurised to reseal the tube length 48.

In operation, both spaces 47 and 51 may be unpressurised simultaneously periodically to permit gas blow back through the valve to clear the valve of any accumulation of ash adhering to the interior surfaces. In a typical operation, the valve is operated once every thirty seconds to deliver a quantity of ash from the cyclone sampler to the batch weighing apparatus 14 (FIG. 1) and may be opened once every five minutes or so to permit blow-back.

Figure 6:
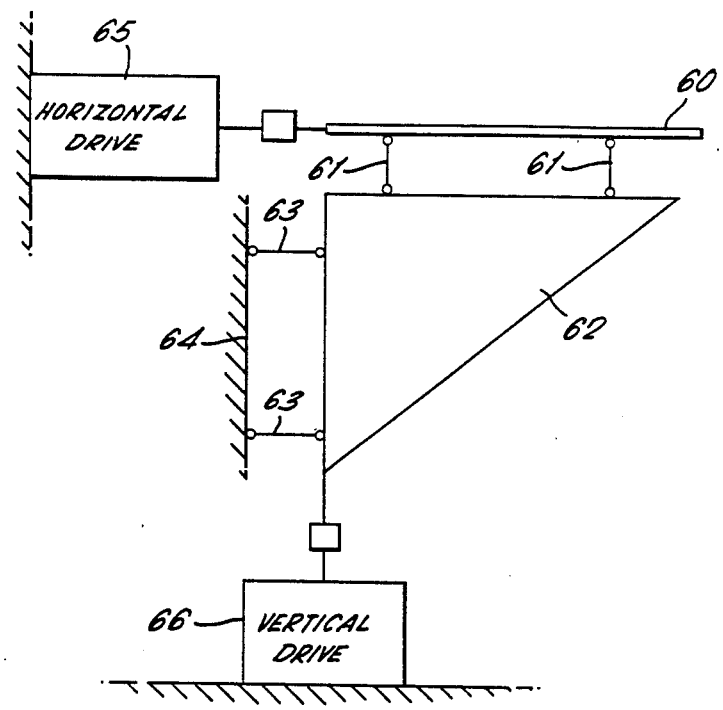
FIG. 6 is a schematic representation of the mounting and drive arrangement of the vibratory table employed in the apparatus of FIGS. 1 and 2.

FIG. 6 illustrates schematically the arrangement for mounting the vibratory table or tube 15 illustrated and described in FIG. 1. In FIG. 6 the tube 15 is illustrated diagrammatically by a flat elongate table 60 which is mounted horizontally by means of parallel links 61 to an intermediate support 62. This mounting arrangement permits the table 60 to move with oscillatory motion substantially parallel to the elongate axis of the table, which is itself arranged horizontally.

Figure 7:
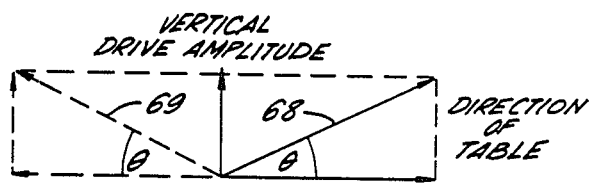
FIG. 7 is a vector diagram illustrating the resultant motion of the table of FIG. 5.

The intermediate support 62 is on the otherhand itself mounted by means of a pair of parallel links 63 to a fixed support 64 which is made rigid with the frame work of the cabinet of the apparatus illustrated in FIG. 1. The links 63 are of equal length and arranged vertically one above the other so that the intermediate support 62 can peform an oscillatory motion only in a vertical direction relative to the fixed support 64. Horizontal vibratory drive 65 and vertical vibratory drive 66 are provided to vibrate the table 60 relative to the intermediate support 62 and the intermediate support 62 relative to the fixed support 64. The drives 65 and 66 produce respective oscillatory motions at a common frequency, but the relative phase of the two oscillations can be selectively reversed. FIG. 7 is a vector diagram illustrating the effect of the combined oscillatory motion on the resultant motion of the table 60. The vector 68 represents the resultant motion of the table 60 when the horizontal and vertical drives 65 and 66 are operated in phase, whereas the dotted vector 69 represents the resultant motion when the horizontal drive is reversed in phase relative to the vertical drive.

The resultant motion 68 has the effect of transporting particulate material on the table 60 along the table to the right, in FIGS. 6 and 7, whereas the resultant motion 69 conveys material to the left. In operation, the quantity of ash delivered to the table from the air lock valve 13 is initially transported to the right to be collected in the bucket 19 of the balance arm 18. A control system detects the balance arm swinging from the collecting position and responds by switching the phase of the vibratory table so that remaining ash thereon is subsequently transported to the left to go to waste.

Figure 8:
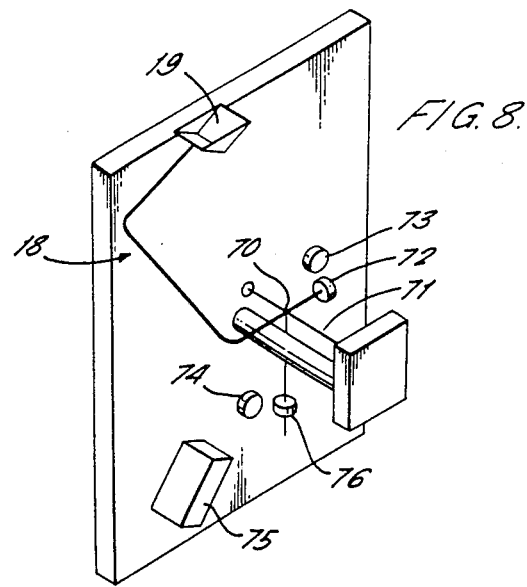
FIGS. 8 and 9 illustrate two forms of batch weigher as may be incorporated in the apparatus of FIGS. 1 and 2.

FIG. 8 illustrates the balance arm arrangement for weighing out the batched of ash to be delivered to the furnace. The balance arm is formed as a double cranked cantilever as illustrated in FIG. 8 which is pivoted at a point 70 on a phosphor bronze suspension strip .71 held under a predetermined tension. The cranked shape illustrated, permits the waste pipe (24 in FIG. 1) to be introduced to collect ash falling from the end 17 of the vibratory table when the bucket 19 swings away.

A first counterbalance 72 provided at the end of the balance arm opposite to the bucket 19 holds the balance arm 18 in the position as illustrated when the bucket 19 is empty and until the bucket has collected the predeteremined mass of ash, whereupon the centre of gravity of the arm crosses over the balance point 70 causing the arm to swing downwards, thereby increasing the moment about the pivot. The swing of the balance arm 18 is arrested after about 90° when the contents of the bucket 19 are ejected into the funnel 21 (FIG. 1).

Proximity switches 73 and 74 detect the position of the balance arm and indicate when the balance arm begins to swing with the required mass of ash in the bucket 19. Accordingly the vibratory table controller is responsive to the proximity switches to reverse the mode of vibration and direction of transport of ash on the table.

An electron-magnet 75 is energised to hold the balance arm in the down position when the ash has been ejected from the bucket 19 until a fresh batch of ash is required, whereupon the electro-magnet 75 is de-energised to release the balance arm which swings back up again under the influence of the second counterweight 76.

Figure 9:
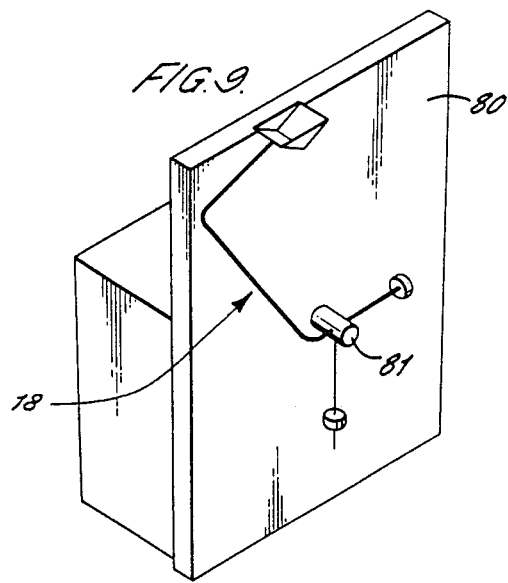

FIG. 9 illustrates an alternative embodiment of the balance arm mechanism using air bearings mounted behind a main bulkhead panel 80. An appropriate form of air bearing is type number A010 available from Horstmann Gauge and Metrology Ltd. of Bath. The air bearing has proved to be more rugged than the suspension strip bearing of FIG. 8. In FIG. 9, the balance arm 18 is mounted on a shaft 81 extending through the main bulkhead panel 80 from the air bearing itself mounted behind the panel. The continuation of the shaft 81 on the reverse side of the bulkhead panel 80 enables the proximity switches and hold electro-magnets to be mounted also behind the panel 80, thereby keeping these components clear of the ash flow. Ash accumulation on the magnet 75 and proximity switches 73 and 74 can interfere with the proper operation of the embodiment shown in FIG. 8.

Figure 10:
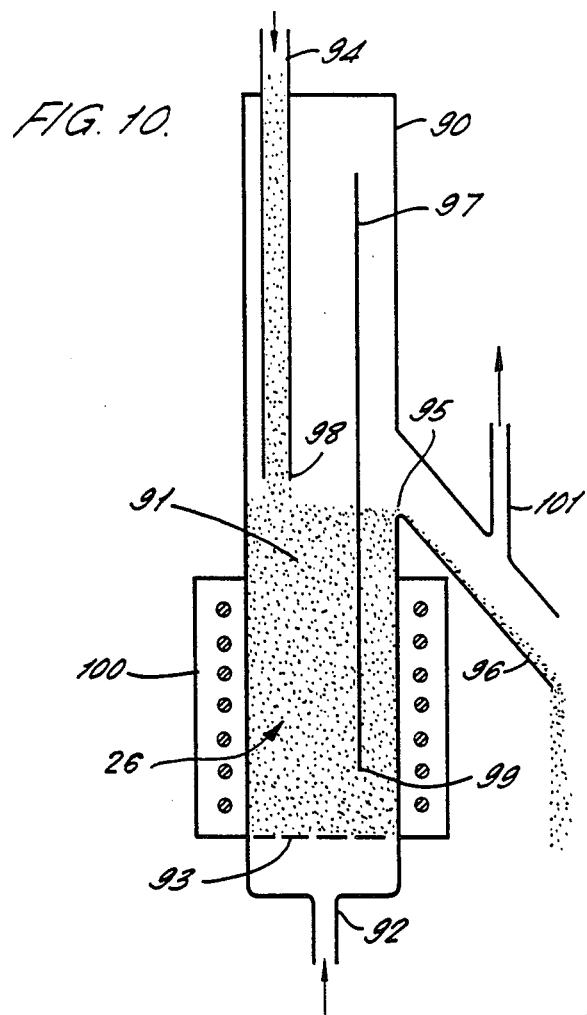
FIG. 10 is a schematic representation of a fluidised bed as may be incorporated in the apparatus of FIGS. 1 and 2.

FIG. 10 illustrates the fluidised bed 26 in diagrammatic form. The fluidised bed 26 comprises an enclosed chamber 90 containing a bed of ash 91 which is fluidised by an upward flow of air pumped into the base of the chamber at inlet 92 and passing through a porous grate 93. The grate 93 is preferably a sintered silica element which has a high flow resistance and reduces channelling effects in the bed. Additional batches of ash are received via the air lock valve 25 (FIG. 1) along an inlet pipe 94 which deposits the batch at the surface of the bed. A weir 95 permits excess ash to flow from the fluidised bed to waste along an inclined section 96 of waste pipe 29 shown in FIG. 1, thereby maintaining the fluidised bed at a substantially constant level within the chamber 90. A baffle plate 97 is mounted within the chamber 90 at a position between the lower end 98 of the delivery tube 94 and the weir 95 so as to prevent carbon containing ash just deposited onto the surface of the bed from flowing direclty to the weir 95 before the carbon is burnt. Ash flowing over the weir 95 has to pass beneath the lower edge 99 of the weir. The weir 97 also extends upwards near to the top of the chamber 90 to minimise the risk of "splashes" of unburnt ash leaving the chamber before being burnt.

An electric muffle furnace 100 surrounds the fluidised bed to maintain the bed at a temperature sufficient to cause combustion of any carbon in the ash delivered to the bed. Temperatures in the range 750° to 900° C. can be used. A convenient temperature is about 800° C. Preferably a temperature sensor, not shown in FIG. 10, is included within the body of the fluidised bed 91 for the automatic control of the bed temperature. Excessive bed temperatures can result in sintering of ash in the bed, whereas temperatures which are too low do not cause complete combustion of carbon contained in the ash.

Carbon dioxide evolved in the burning of carbon in the fluidised bed flows with the fluidising gas over the top of the baffle 97 and down the outlet pipe 96. A sample is withdrawn along a pipe 101 for delivery to a $CO_2$ analyser. The $CO_2$ analyser monitors the $CO_2$ concentration in the gas leaving the fluidised bed.

It is important that the volume flow rate of fluidising gas to the fluidised bed, as delivered at the inlet 92, is kept accurately constant, so that the $CO_2$ concentration obtained from the $CO_2$ analyser provides an accurate representation of the amount of carbon being burnt in the bed.

Figure 11:
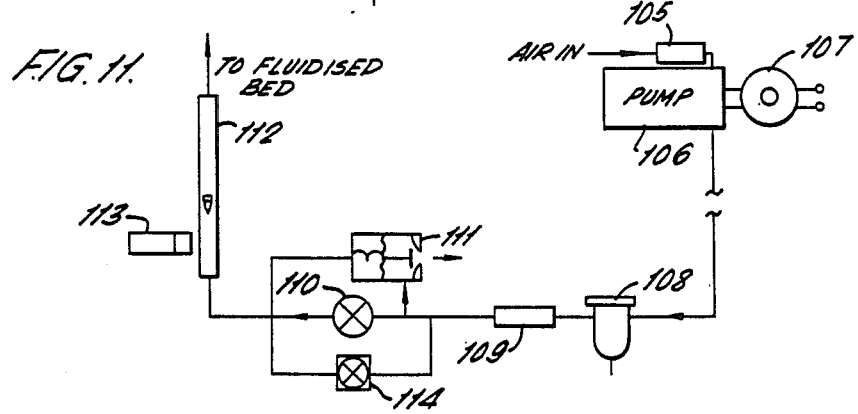
FIG. 11 is a schematic diagram of the apparatus for providing and controlling the flow of fluidising air through the fluidised bed.

FIG. 11 illustrates diagrammatically the system for supplying the fluidising air. Air is drawn through a first filter 105 by means of a pump 106 controlled by a variable transformer 107, and delivered via a coarse filter and water trap 108 and, a further fine filter 109 to a main control valve 110. A constant volume flow of gas through the control valve 110 is maintained by a flow regulator 111 connected in parallel around the valve 110 to maintain the pressure drop across the valve substantially constant. A flow meter 112 enables the rate of flow to be monitored visually and an automatic switch 113 provides an indication if the flow rate drops below a minimum level.

An additional solenoid valve 114 is provided in parallel with the main control valve 110 and enables a boost of air at higher volume flow to be delivered to the fluidised bed at intervals. For example a one second pulse of air at a flow rate about five times the normal may be give every thirty seconds, to provide additional agitation to the fluidised bed to maintain fluidisation when certain ashes are being monitored.

Figure 12:
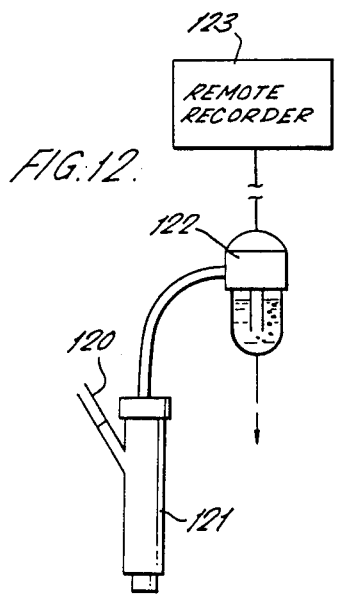
FIG. 12 is a schematic representation of a $CO_2$ analyser which may be employed with the apparatus of FIGS. 1 and 2.

FIG. 12 illustrates the $CO_2$ analyser which is arranged to draw sample gas from the outlet pipe 101. The analyser is connected to the union 28 in FIG. 1. The sample is fed to the analyser by an inlet pipe 120 and is initially filtered in filter 121 to remove dust. The filtered gas sample is passed to the $CO_2$ analyser 122. Any suitable form of $CO_2$ analyser may be employed which has a response time comparable with the response time of the carbon-in-ash monitor as a whole. Response times of about sixty seconds for the $CO_2$ analyser have been found satisfactory.

The output signal from the $CO_2$ analyser is fed to a penrecorder 123, which may be remotely located, to keep a permanent record of the reading.

The apparatus contained in the cabinet 10, as illustrated in FIG. 1, may all be automatically controlled by a remote electronic controller. The electronic controller is preferably located remotely from the cabinet so that the cabinet itself can operate at a relatively high temperature which improves the flow characteristics of the ash. Electronic control signals and electrical supplies are fed to the cabinet along signal lines 130. Similarly, the pneumatic control of the two air lock valves 13 and 25 is provided by control air lines 131 and air supplied for the fluidising air for the fluidised bed 26, and for the air bearing of the balance arm 18 may be supplied along air line 132.

As mentioned previously, the control system may control the apparatus to operate with a thirty second cycle time for delivery of batches of ash to the fluidised bed 26. The sequence of operations may be as follows. Once thirty seconds have passed since the last batch of ash was delivered to the fluidised bed, the electro-magnet holding the balance arm 18 down is de-energised releasing the balance arm to receive further ash from the vibratory table 15. At the same time, the air lock valve 13 is operated to deliver a quantity of ash to the vibratory table 15 and the mode of vibration of the table is set to transport the ash to the right towards the balance arm bucket. When the bucket contains the required mass of ash, the balance arm swings away operating the proximity switch to signal the control system to reverse the direction of transport of the vibratory table 15. The next batch of ash is duly tipped out of the bucket 19 into the funnel 21, the balance arm 18 being held down by re-energising of the electro-magnet. The air lock valve 25 is then operated to deliver the batch to the fluidised bed. The process is then repeated at thirty second intervals. The thirty second cycle time is selected to ensure that each batch of ash delivered to the fluidised bed is completely burnt before the next batch, to avoid a gradual build up in the carbon level in the fluidised bed. However it is important that the overall mass rate of delivery of ash to the fluidised bed is constant, so that together with the constant volume flow rate of air to the bed, the concentration of carbon dioxide in the gas leaving the bed is a true indication of the amount of carbon contained in the ash.

In the above mode of operation, it is possible for the quantity of ash delivered to the vibratory table 15 in a particular cycle to be inadequate to form a complete batch. Then the quantity will be completely delivered to the bucket of the balance arm without causing the balance arm to swing away and operate the proximity switch. Only when the next successive cycle is initiated is further ash supplied to the table and subsequently delivered to the bucket to complete the required batch. This results in a batch being lost, which would cause an apparently reduced $CO_2$ reading.

The apparatus may be arranged to compensate for batches lost in this way by recording the number of batches lost in an accounting period of say 5 minutes. A processing unit receives data defining the measured $CO_2$ readings from successive batches at the normal 30 second intervals and averages these over the accounting period. This average value, together with the actual number of batches in the period, is used to calculate the carbon-in-ash value for the accounting period.

In another embodiment of the invention, it is possible to dispense with the balance arm mechanism 18. Instead, the accelration amplitude of the vibratory table 15 is monitored. It will be appreciated that with a constant driving force applied to vibrate the table, the acceleration amplitude is dependent on the mass of the table and any load of ash thereon. The acceleration amplitude of the table may be measured by accelerometers mounted on the table, or by displacement sensors providing signals proportional displacement of the table which can then be twice differentiated to provide signals representing acceleration.

Instead the drive voltages and/or currents to the vibratory drivers may be monitored and used to develop a signal representing acceleration amplitude.

To improve the sensitivity of detecting changes in the acceleration amplitude, the signals from the acceleration sensors are filtered to a pass band immediately around the driving frequency of the vibrators. Furthermore, the vibration frequency is made substantially different from the frequencies of unwanted vibrations likely to occur elsewhere in the instrument and in the surrounding environment. Additionally the vibratory feeder mechansim is itself mounted on an anti-vibration mount to reduce the level of high frequency vibrations introduced into the feeder from the outside environment.

It is possible to obtain a discrimination of better than 0.025 gram in determining the mass of ash delivered from the vibratory table. This represents an accuracy of 10% in measuring batches of ash of 0.25 gram.

In operation the control system is arranged initially to detemine the acceleration amplitude level of the table alone, with no load of ash. The air lock valve 13 is then operated to deposit a quantity of ash on the table and the change in acceleration of the table then monitored to determine the mass of the total sample from the valve.

The vibratory mode of the table is then set to deliver ash to a delivery end of the table until the acceleration amplitude has increased again to a level indicating that the desired mass of ash has been delivered in the current batch. The vibratory mode of the table is then reversed so that remaining ash in the sample on the table is transported to the other end of the table to waste.

Figure 13:
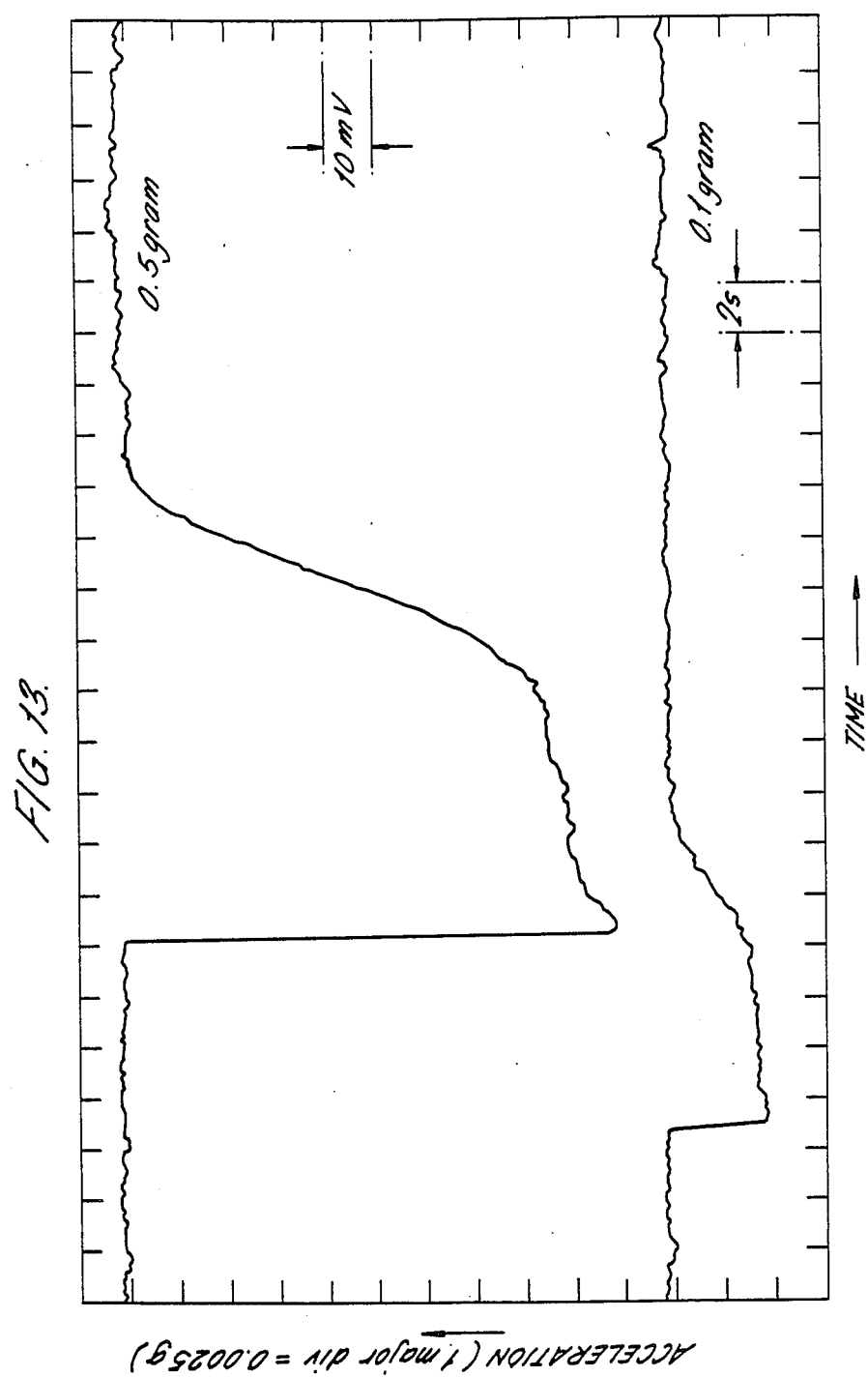

FIG. 13 is a graphical illustration of the response of the acceleration amplitude as measured with time as a known mass of ash is deposited on a vibratory table and the progressively falls off one end of the table. The upper trace indicates the effect of depositing a sample of 0.5 gram of ash on the table, corresponding to the downward step in the graph followed by a gradual return to the initial level as the ash falls off one end of the table. The lower trace is a similar representation when a quantity of 0.1 gram is deposited. From these traces it can be seen that a discrimination of better than 0.025 gram is possible. This level of discrimination is sufficient to measure batches of ash of 0.25 grams to an accuracy of ±10%.

Figure 14:
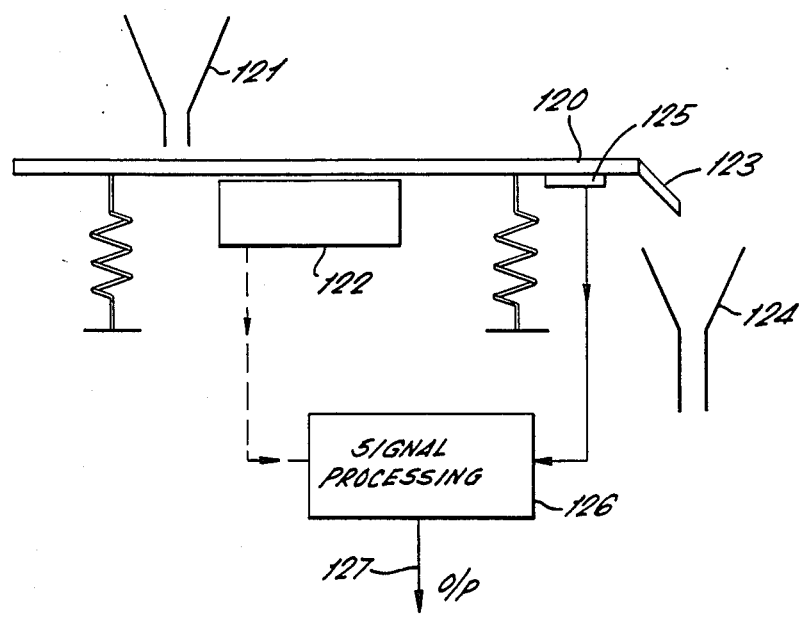
FIG. 14 is a schematic representation of an embodiment of batch weigher operative in accordance with the graphical representation of FIG. 13.

FIG. 14 illustrates schematically a batch weigher operating as described above. Particulate material to be batched is supplied to a vibratory table 120 from a supply funnel 121. The table 120 is driven by a transducer 122 so as to transport the material towards a delivery chute 123 for collection in a collection funnel 124. An accelerometer 125 is fixed to the table 120 and supplies a signal representing the acceleration of the table to a signal processing unit 126. The signal processing unit 126 produces an output signal on a line 127 which, in one mode of operation represents the mass of the batch of material delivered from the chute 123. The signal processing unit 126 may be arranged firstly to record the accelertion amplitude of the table when empty. A charge of the particulate material is then supplied from the funnel 121 causing a reduction in acceleration amplitude. The unit 126 may measure this reduction and determine therefrom the mass of the charge of material supplied to the table. If the entire charge is in due course transported by the table and delivered from the chute 123, the unit 126 may produce a signal on line 127 representing the mass of the charge, which in turn then represents the mass of the batch delivered from the table.

In another mode of operation, the signal processing unit 126 may monitor the increase in measured acceleration from the minimum level as material is progressively discharged by the chute 123. In this way an output signal on line 127 may be generated when the monitored increase in acceleration is indicative of a predetermined mass of material having been discharged from the chute 123. Further collection of material by funnel 124 may then be terminated to define a batch of the required mass.

We claim:

1. Apparatus for monitoring the carbon content of boiler flue ash comprising ash receiving means to receive ash sampled from a boiler flue, a fluidised bed furnace constructed and arranged to burn any carbon in ash received therein to evolve carbon dioxide, gas flow means to provide a measured flow rate of fluidising gas to the fluidised bed furnace, a carbon dioxide analyser providing an indication of carbon dioxide concentration, feeding means to feed gas including evolved carbon dioxide from the fluidised bed furnace to the analyser, and batching means to deliver batches of ash of measured mass to the furnace at a measured frequency, the batching means including a vibratory table for transporting ash between a point of supply of ash to the table from the ash receiving means to a point of delivery of ash in a stream from the table, and collecting means for collecting a stream of ash to provide batches of ash, wherein said vibratory table is horizontal in the direction of transport and includes direction selecting means to change the mode of vibration of the table to reverse the direction of transport of ash on the table.

2. Apparatus as claimed in claim 1 further comprising waste receiving means on a side of the supply point remote from said delivery point, said waste receiving means positioned to receive ash during said reversed direction of transport, for collection from the table.

3. Apparatus as claimed in claim 1 wherein said vibratory table comprises a horizontal delivery table, and intermediate support, first mounting means mounting the table on the intermediate support for oscillatory movement of the table relative to the intermediate support only in a first substantially linear direction parallel to the delivery direction, a fixed support, second mounting means mounting the intermediate support on the fixed support for oscillatory movement of the intermediate support relative to the fixed support only in a second substantially linear direction in a vertical plane and orthogonal to said first direction, vibrating means to apply said oscillatory movements at a common frequency, and control means for changing the relative phase of the oscillatory movements to reverse the direction of transport.

4. Apparatus as claimed claim 1 and including acceleration responsive means providing an indication of the acceleration amplitude of the vibratory table, and means determining the difference in said indication between the start and finish of delivery from the table of a batch of ash collected in said collecting means to measure the mass of the batch.

5. Apparatus as claimed in claim 1 wherein said batching means comprises means for determining when a predetermined mass of ash, representing one batch of measured mass, is collected in said collecting means and, in response thereto, halting further collection of ash in the collecting means.

6. Apparatus as claimed in claim 5 wherein said means for determining is effective to operate said direction selecting means to reverse the direction of transport when a predetermined mass of ash is collected in said collecting means.

7. Apparatus as claimed in claim 1 and including air lock means to deliver ash from the ash receiving means to the batching means.

8. Apparatus as claimed in claim 7 wherein the air lock means is constituted by an air lock valve comprising first and second lengths of flexible tube in series and fluidly connected via a connecting means to conduct ash by gravity from the receiving means to the batching means, the first length being located above the second length; an outer housing defining respective closed annular spaces around the first and second lengths of tube whereby fluid pressure within one of the annular spaces can collapse the respective length of tube to seal the length; and means for applying said fluid pressure to the two annular spaces alternately so that one length of tube is always sealed.

9. Apparatus as claimed in claim 8 and including a further said air lock means positioned and arranged to deliver measured batches from said batching means to the furnace.

10. Apparatus as claimed in claim 8 wherein each of said lengths of flexible tube is formed to be noncircular in cross-section.

11. Apparatus as claimed in claim 10 wherein said lengths of tube have a first transverse dimension which is greater than a second orthogonal transverse dimension.

12. Apparatus as claimed in claim 11 wherein the lengths of tube are formed to have cross-sections with diametrically opposed acute angle internal corners, whereby the lengths of tube can collapse flat under external fluid pressure to completely seal the respective length

* * * * *

UNITED STATES PATENT AND TRADEMARK OFFICE
CERTIFICATE OF CORRECTION

PATENT NO. : 4,775,516

DATED : October 4, 1988

INVENTOR(S) : Roger D. Kempster et al.

It is certified that error appears in the above-identified patent and that said Letters Patent is hereby corrected as shown below:

IN THE BACKGROUND OF THE INVENTION

In column 1, line 24, please delete "Rd" and substitute therefor --D--.

IN THE BRIEF SUMMARY OF THE INVENTION

In column 2, line 25, after "from" please insert --the--.

IN THE BRIEF DESCRIPTION OF THE DRAWINGS

In column 5, line 27, please delete "12" and substitute therefor --13--.

IN THE DESCRIPTION OF
THE PREFERRED EMBODIMENTS

In column 6, line 2, please delete "inthe" and substitute therefor --in the--.

In column 8, line 14, please delete "peform" and substitute therefor --perform--.

UNITED STATES PATENT AND TRADEMARK OFFICE
CERTIFICATE OF CORRECTION

PATENT NO. : 4,775,516
DATED : October 4, 1988
INVENTOR(S) : Roger D. Kempster et al.

It is certified that error appears in the above-identified patent and that said Letters Patent is hereby corrected as shown below:

In column 8, line 42, please delete "batched" and substitute therefor --batches--.

In column 8, line 67, please delete "electron-magnet" and substitute therefor --electro-magnet--.

In column 9, line 36, after "bed" please insert --26--.

In column 9, line 41, please delete "direclty" and substitute therefor --directly--.

In column 10, line 21, please delete "give" and substitute therefor --given--.

In column 11, line 36, please delete "accelration" and substitute therefor --acceleration--.

UNITED STATES PATENT AND TRADEMARK OFFICE
CERTIFICATE OF CORRECTION

PATENT NO. : 4,775,516
DATED : October 4, 1988
INVENTOR(S) : Roger D. Kempster

It is certified that error appears in the above-identified patent and that said Letters Patent is hereby corrected as shown below:

In column 11, line 43, after "proportional" please insert --to the--.

In column 11, line 57, please delete "mechansim" and substitute therefor --mechanism--.

In column 12, line 14, please delete the first occurrence of "the" and substitute therefor --then--.

In column 12, line 38, please delete "accelertion" and substitute therefor --acceleration--.

IN THE CLAIMS

In column 13, line 19, please delete "and" and substitute therefor --an--.

In column 13, line 34, after "claimed" please insert --in--.

UNITED STATES PATENT AND TRADEMARK OFFICE
CERTIFICATE OF CORRECTION

PATENT NO. : 4,775,516
DATED : October 4, 1988
INVENTOR(S) : Roger D. Kempster

Page 4 of 4

It is certified that error appears in the above-identified patent and that said Letters Patent is hereby corrected as shown below:

In column 14, line 2, after "thereto," please insert --for--.

In column 14, line 42, please insert --.--.

Signed and Sealed this

First Day of January, 1991

Attest:

HARRY F. MANBECK, JR.

Attesting Officer

Commissioner of Patents and Trademarks